(12) United States Patent
Temme

(10) Patent No.: US 11,395,900 B2
(45) Date of Patent: Jul. 26, 2022

(54) TRANSPORTABLE DEVICE, SYSTEM AND METHOD FOR PROVIDING A COOLED, OXYGEN-CONTAINING GAS FLOW

(71) Applicant: Fabian Temme, Gütersloh (DE)

(72) Inventor: Fabian Temme, Gütersloh (DE)

( * ) Notice: Subject to any disclaimer, the term of this patent is extended or adjusted under 35 U.S.C. 154(b) by 644 days.

(21) Appl. No.: 16/331,782

(22) PCT Filed: Sep. 9, 2017

(86) PCT No.: PCT/EP2017/001065
§ 371 (c)(1),
(2) Date: May 23, 2019

(87) PCT Pub. No.: WO2018/046128
PCT Pub. Date: Mar. 15, 2018

(65) Prior Publication Data
US 2020/0164173 A1    May 28, 2020

(30) Foreign Application Priority Data
Sep. 9, 2016 (LU) .......................................... 93200

(51) Int. Cl.
*A61M 16/10* (2006.01)
*A61M 16/20* (2006.01)
*A61M 16/12* (2006.01)

(52) U.S. Cl.
CPC ........ *A61M 16/1075* (2013.01); *A61M 16/12* (2013.01); *A61M 16/201* (2014.02);
(Continued)

(58) Field of Classification Search
CPC ............ A61M 16/1075; A61M 16/201; A61M 16/12; A61M 2205/3626; A61M 2205/3605; A61M 2205/366
See application file for complete search history.

(56) References Cited

U.S. PATENT DOCUMENTS 5,261,399 A    11/1993   Klatz et al.
5,957,964 A     9/1999   Ceravolo
(Continued)

FOREIGN PATENT DOCUMENTS

DE    102007019616 A1    10/2008
WO       2003047603 A2     6/2003
(Continued)

OTHER PUBLICATIONS

International Search Report in corresponding PCT Application No. PCT/EP2017/001065, dated Feb. 12, 2018.

*Primary Examiner* — Margaret M Luarca
(74) *Attorney, Agent, or Firm* — Andrus Intellectual Property Law, LLP

(57) ABSTRACT

The present disclosure relates to a transportable device for providing a cooled, oxygen-containing gas flow for supplying to a body of mammal via the respiratory tract, in particular a human being, in order to lower the body temperature. The device comprises a storage device comprising at least one fluid reservoir and at least one heat exchanger, wherein the storage device is designed to store an oxygen-containing fluid in the fluid reservoir and for providing a discharge flow of the oxygen-containing fluid. The heat exchanger is designed to cool the provided discharge flow by transferring heat to a cooling stream of a stored fluid and provided by the storage device, and a cooled, oxygen-containing gas flow for supplying to the body emerges from the heat exchanger.

13 Claims, 6 Drawing Sheets

(52) U.S. Cl.
CPC ............... *A61M 2202/0208* (2013.01); *A61M 2202/0275* (2013.01); *A61M 2202/03* (2013.01); *A61M 2205/3368* (2013.01); *A61M 2205/3606* (2013.01); *A61M 2205/366* (2013.01); *A61M 2205/3626* (2013.01)

(56) References Cited

U.S. PATENT DOCUMENTS

| | | |
|---|---|---|
| 7,201,163 B2 | 4/2007 | Jiang et al. |
| 2008/0262377 A1 | 10/2008 | Belson |
| 2010/0108063 A1 | 5/2010 | Koch et al. |
| 2010/0307635 A1* | 12/2010 | Holder ................. F17C 5/06 141/4 |
| 2012/0031405 A1 | 2/2012 | Geist et al. |
| 2014/0338668 A1 | 11/2014 | Eum |
| 2015/0151073 A1 | 6/2015 | Shushunov |
| 2017/0143538 A1* | 5/2017 | Lee ..................... A61F 7/12 |

FOREIGN PATENT DOCUMENTS

| | | |
|---|---|---|
| WO | 2004082729 A2 | 9/2004 |
| WO | 2011115964 A1 | 9/2011 |
| WO | 2013079227 A1 | 6/2013 |
| WO | 2013090730 A1 | 6/2013 |

\* cited by examiner

TRANSPORTABLE DEVICE, SYSTEM AND METHOD FOR PROVIDING A COOLED, OXYGEN-CONTAINING GAS FLOW

CROSS-REFERENCE TO RELATED APPLICATIONS

This application is the U.S. national stage application of International Application No. PCT/EP2017/001065, filed Sep. 9, 2017, which International Application was published on Mar. 15, 2018, as International Publication WO 2018/046128 A1 in the German language. The International Application claims priority to Luxembourg Application No. LU 93200, filed Sep. 9, 2016. The International Application and Luxembourg Application are both incorporated herein by reference, in their entireties.

FIELD

The present disclosure relates to a transportable device and a method for providing a cooled, oxygen-containing gas flow for supply to a body of a mammal via the respiratory tract, in particular of a human being, in order to lower the body temperature. The present disclosure further relates to a system having at least one device of the aforementioned type. In addition, the present disclosure relates to a method for lowering the body temperature of a mammal, in particular a human being, via the respiratory tract by means of a cooled, oxygen-containing gas.

BACKGROUND

It is known that every year a great many people suffer a stroke. A stroke, also called a cerebral stroke, is the result of reduced blood flow to the brain of the person affected, as a result of which brain cells may die. A distinction may be made between two types of stroke. An ischemic stroke is triggered by a reduced blood flow. A hemorrhagic stroke is the term used when the blood circulation is reduced and/or interrupted on account of bleeding from damaged or burst blood vessels or damaged tissue.

The function of the brain or of parts of the brain may be impaired by both types of stroke. Symptoms of a stroke can include restricted movement or a feeling of numbness on one side of the body. Those affected may have problems speaking, or their hearing may be impaired. Vision may be limited, and the individual affected may suffer from dizziness. If the symptoms disappear after less than one or two hours, the condition is referred to as a mini stroke.

The symptoms of a stroke may be permanent. The long-term consequences can include inflammation of the lungs and loss of urinary control.

In the event of a stroke, it is therefore of great importance to avoid or at least reduce these symptoms, i.e. to protect the organs such as the brain and heart in order to save the patient's life and at the same time to avoid or minimize the long-term consequences. The oxygen saturation of the tissue is of great importance in achieving these goals. According to current medical guidelines (DEGAM Guidelines 8, 2012), it is essential, in the event of a stroke, to ensure first of all that the patient's airways are kept free. Next, the patient should be placed in a comfortable position and supplied with oxygen, an intravenous access should be established, and blood pressure and blood glucose levels should be measured.

It is also known that cooling the tissue advantageously reduces the oxygen consumption.

U.S. Pat. Nos. 5,261,339 A and 5,957,964 A describe cooling the tissue of a patient, on the one hand by means of a helmet that cools the head externally, and, on the other hand, by the use of a precooled infusion.

From U.S. Pat. No. 7,201,163 B2 and DE 10 2007 019 616 A1, it is known that reducing the body temperature can also be done via the respiratory tract. While U.S. Pat. No. 7,201,163 B2 discloses the delivery of humidified, atomized air, DE 10 2007 019 616 A1 describes the delivery of a liquefied gas as cooling medium into the respiratory tract.

Despite the known forms of therapy, the long-term consequences for patients cannot always be avoided, for example because the treatment can only take place in a hospital and the transport to the latter takes up crucial time.

In this connection, WO 2011/115964 A1 discloses a system for therapeutic cooling of regions of the body, for example the brain. In this case, a gas emerging from an oxygen container undergoes adiabatic cooling and in this state is delivered to the airways of a patient.

US 2008/0262377 A1 discloses a method and a device for controlling the body temperature of a patient. A respiratory gas mixture is in this case heated or cooled by means of a heating and/or cooling device. The gas used can be air or a special respiratory mixture, for example a mixture of helium and oxygen. In order to further increase the rate of heat transfer, the system can comprise an ice particle generator for introducing fine ice particles into the flow of the respiratory gas.

US 2012/0031405 A1 describes a brain-cooling system, which comprises a gas-dispensing system and a cooling device. The gas-dispensing system can generate a desired pressure and a flow rate for gases that are to be inhaled by a patient. The cooled respiratory gases can be delivered to the patient with an elevated oxygen fraction and at an elevated air pressure exceeding a normal physiological air pressure.

WO 2013/079227 A1 describes a device with which the brain of a patient who suffers a cardiovascular emergency can be cooled by an intranasal route. The device comprises a cannula for insertion into the airways of the patient, wherein a gas that has cooled upon adiabatic expansion is supplied to the patient.

SUMMARY

One object of the present disclosure is to make available a device, a method and a system, each of the aforementioned types, which in an effective and simple way permit the provision of a cooled, oxygen-containing gas flow for therapeutic treatment of a human or animal patient, in particular for reducing and/or improving the long-term sequelae of a stroke.

The aforementioned object is achieved by a device having the features of claim 1, a system having the features of claim 11, a method having the features of claim 12, and a method having the features of claim 13. Advantageous embodiments of the present disclosure are the subject matter of the subclaims.

According to the present disclosure, a transportable device is proposed for providing a cooled, oxygen-containing gas flow for supply to a body of mammal via the respiratory tract, in particular of a human being, in order to lower the body temperature. The device according to the present disclosure has a storage unit, comprising at least one fluid reservoir, and at least one heat exchanger, wherein the storage unit is designed to store an oxygen-containing fluid in the fluid reservoir and to provide a gaseous or liquid discharge flow of the oxygen-containing fluid, wherein the heat exchanger is designed to cool the provided discharge flow by transfer of heat to a cooling stream of a stored fluid likewise provided by the storage unit, and wherein a cooled, oxygen-containing gas flow for supply to the body emerges from the heat exchanger.

In one embodiment of the method according to the present disclosure, provision is made that an oxygen-containing fluid is stored in the fluid reservoir, and a discharge flow of the oxygen-containing fluid is provided, wherein the discharge flow is cooled with a cooling flow in order to obtain a cooled, oxygen-containing gas flow with a preferably defined temperature for supply to the body. According to the present disclosure, in order to provide a cooled, oxygen-containing gas at a defined temperature below body temperature, a cold and preferably liquefied gas is heated in a first subsidiary stream and then mixed with a second, cold bypass stream, as a result of which the temperature of the gas can be subject to open-loop and/or closed-loop control.

Provision can be made for the oxygen-containing fluid to be stored in liquid form, wherein a discharge flow of the oxygen-containing fluid is provided from the storage unit in a liquid or gaseous state and deep cold and, before being supplied to a patient, is first of all heated to a defined temperature. For this purpose, a preheater or an atmospheric vaporizer can be provided from which the heated discharge flow emerges. In order thereafter to cool the discharge flow to a defined, therapeutically effective lower temperature, the present disclosure provides that the heated discharge flow is cooled with a cooling stream of a stored fluid likewise provided from the storage unit. A corresponding situation applies when the oxygen-containing gas is stored at high pressure, wherein there is a marked decrease in temperature upon adiabatic expansion of the gas as it emerges from the fluid reservoir. In order in this case to ensure a defined, low temperature of the gas for supply to a patient, it may be necessary to initially heat the cold gas after the expansion and then cool the gas again to a defined temperature below body temperature.

The fundamental concept of the present disclosure is that a discharge flow of an oxygen-containing fluid provided from the storage unit is cooled by means of a second, colder cooling stream, likewise made available from the storage unit, by direct and/or indirect transfer of heat to the cooling stream, such that a cooled, oxygen-containing gas flow with a defined temperature is obtained as respiratory flow for supply to the body of a patient. In particular, the present disclosure thus makes it possible to easily set an advantageous temperature of the gas flow for supply to a body or to control and/or regulate the temperature of the gas flow, such that long-term sequelae of a stroke can be prevented or at least attenuated by the gas supply. Also of advantage for successful treatment is the fact that, since the discharge flow of the oxygen-containing fluid provided according to the present disclosure is cooled by the second, colder cooling stream, the temperature of the discharge flow can be kept more or less constantly at a predefined temperature level. In addition to treatment of a stroke patient, the device according to the present disclosure is also suitable for treating and reducing the long-term sequelae in patients with intracranial trauma, concussion or heatstroke. Moreover, lowering of the body temperature also has a positive effect on survival chances during resuscitation, since the oxygen requirement of the patient is reduced.

With the device according to the present disclosure, a cooled, oxygen-containing gas flow for supply to the body at a defined low temperature suitable for therapy can be made available in a simple and cost-effective manner, and temperature fluctuations resulting from environmental influences, for example on account of high ambient temperatures in the summer, can be reduced or eliminated by means of the discharge flow from the fluid reservoir being cooled by a colder fluid. In this way, the patient is reliably supplied with a constantly cooled, oxygen-containing gas flow. Of course, the temperature of the cooled, oxygen-containing gas flow lies below the body temperature of the patient in order to achieve a therapeutic effect. The temperature of the gas flow supplied to the patient is preferably less than 5° C., more preferably less than 0° C., advantageously between −10° C. and −32° C.

If a patient suffers a stroke, emergency service personnel such as ambulance crews or emergency physicians are easily able to carry the transportable device according to the present disclosure around with them. For example, the device can be transported over long distances in an ambulance or rescue helicopter. In addition, the device is also suitable to be easily carried by a single person. In this way, rapid and early treatment of the patient is also possible away from a hospital.

The storage unit of the device according to the present disclosure can preferably be dimensioned in such a way, or the capacity of the at least one fluid reservoir dimensioned in such a way, that the supply of the discharge flow and/or of the cooling flow is ensured only over a period of a few hours, preferably less than two hours, more preferably less than one hour. Accordingly, the device according to the present disclosure is provided in particular for the initial treatment of a patient. A low storage capacity of the storage unit reduces the weight of the device according to the present disclosure and decreases its overall structural volume, which makes the device easier to transport. Moreover, manufacturing costs can thus be reduced. At the same time, the storage unit has to be big enough to ensure that a patient in an emergency situation can be supplied for a sufficient length of time with a cooled, oxygen-containing gas flow. A sufficient length of time signifies the aforementioned period of a few hours. The transportable device is preferably used in emergency situations in which the supply of a cooled, oxygen-containing gas flow to the patient is preferably intended to be ensured at least until the patient is admitted to a hospital.

The fluid reservoir is preferably configured as a refillable reservoir. By refilling the fluid reservoir, it is then possible for the transportable device to be used several times. Alternatively, replacement of the fluid reservoir is possible.

According to the present disclosure, a respiratory mask is provided for supplying the cooled, oxygen-containing gas flow to the respiratory tract of the patient. Corresponding respiratory masks are known to persons skilled in the art. The respiratory masks can cover parts of the face or can cover the entire face. A mask can provide the gas through the mouth and/or the nose of the patient. For this purpose, the mask can have at least one tube. The respiratory mask ensures a reliable supply of the cooled, oxygen-containing gas flow into the respiratory tract of the patient.

In one embodiment of the present disclosure, an open-loop and/or closed-loop controller is provided. The latter is designed to permit open-loop and/or closed-loop control of the temperature of the cooled, oxygen-containing gas flow supplied to the patient. The open-loop and/or closed-loop control of the temperature is effected by changing the size ratio between the discharge flow and the cooling flow with which the discharge flow from the fluid reservoir is cooled. With the aid of the open-loop and/or closed-loop controller, the temperature of the cooled, oxygen-containing gas flow or of the respiratory flow supplied to the patient can be set to a desired value. At the same time, the temperature of the gas flow can be kept constant in a simple way, even when there are strong and rapid fluctuations in the ambient temperatures. In addition, it is also possible to set a temperature profile of the cooled, oxygen-containing gas flow, which can have a positive influence on the process of cooling a patient's tissue. For example, the body temperature of a patient may be lowered within a short time period in which a low temperature of the cooled, oxygen-containing gas flow is set. Once the desired body temperature of the patient is reached, the lowered body temperature can be maintained by setting a higher temperature of the cooled, oxygen-containing gas flow.

The open-loop and/or closed-loop controller can have an actively and/or passively actuated valve. For example, an electrically switchable valve can be provided as active valve. If use is made of switchable valves, i.e. an open-loop and/or closed-loop controller with at least one active actuator, it is necessary to measure the temperature of the cooled, oxygen-containing gas flow for supply to the body of the patient. Depending on the measured temperatures, the valve is then actively switched. The use of actively switched valves has the disadvantage that energy is required and consumed for the purpose of measuring the temperature, evaluating the temperature and switching the valves. The required energy can be taken, for example, from an electrical store, a Seebeck element and/or a fluid stored in the storage unit.

However, the open-loop and/or closed-loop controller preferably has a passive valve, which is switched via a bimetallic actuator. A bimetallic strip, as called a thermostatic bimetal, is composed of two layers of different materials which are connected to each other by cohesive bonding or by form-fit engagement. A change of temperature causes a change in the shape of the bimetallic strip. This is manifested, for example, as a bending process brought about by different coefficients of thermal expansion of the metals used. If the temperature of the cooled, oxygen-containing gas flow deviates from the target value, the shape of the bimetallic strip adapted to the particular application changes, as a result of which the valve is switched or adjusted and the size of the cooling flow is changed. Through the use of a bimetallic strip as actuator of an open-loop and/or closed-loop controller, it is possible to achieve open-loop and/or closed-loop control of the temperature of the cooled, oxygen-containing gas flow in a simple way. The use of actively switched actuators is then unnecessary, as a result of which the energy consumption or energy requirement and the complexity of the open-loop and/or closed-loop control can be reduced considerably.

In another embodiment of the present disclosure, the cooling flow is formed by a bypass flow of the oxygen-containing fluid stored in the fluid reservoir. The discharge flow and the cooling flow then have the same composition, wherein a heated first mass flow of the stored oxygen-containing fluid is cooled with a second mass flow of the same oxygen-containing fluid (bypass flow) to a defined, lower temperature. According to the present disclosure, two mass flows are then taken from the fluid container, of which one mass flow is used for open-loop and/or closed-loop temperature control of the other mass flow in the sense of a bypass solution. If the cooling is effected by direct heat transfer between the discharge flow and the cooling flow, with substance transfer or mixing together of the two mass flows, it is always possible to achieve the same composition of the respiratory gas supplied to the patient, even when the sizes of the two mass flows are different. At the same time, the open-loop and/or closed-loop temperature control can be simplified, since both mass flows have the same physical properties. In principle, however, the possibility of cooling the discharge flow with a fluid having another composition is not excluded. This makes it possible, for example, to supply a therapeutically active gas component such as a noble gas. The cooling of the discharge flow with a bypass flow, with both mass flows being taken from the same fluid container, leads to a simplified design and permits a compact structure of the device according to the present disclosure. In particular, there is no need for a separate cooling means in order to provide a cooling flow for cooling the withdrawn mass flow of the oxygen-containing gas.

In an advantageous embodiment of the present disclosure, the fluid reservoir contains a deep-cooled, liquefied oxygen-containing fluid, in particular liquid oxygen or liquefied air. In this way, the demands in respect of storage technology are reduced in comparison to storage of compressed gas, and it is possible to dispense with high system pressures.

The fluid reservoir is advantageously insulated in such a way that a deep-cooled, liquefied, oxygen-containing fluid is at a sufficiently low temperature for a sufficient length of time. A sufficient length of time is to be understood as at least two days, preferably at least three days, more preferably at least four days, advantageously seven days.

However, despite the insulation of the fluid reservoir, a transfer of heat from the environment into the fluid reservoir cannot be completely ruled out during low-temperature storage of the oxygen-rich fluid, wherein the internal pressure of the container increases on account of the heat transfer, and a withdrawal of fluid and the supply of the oxygen-rich gas to the patient can take place solely on account of the internal pressure of the container, without additional pressure build-up means such as fans or the like.

In principle, however, it is also not possible to exclude pressure storage, preferably with subsequent adiabatic expansion of the stored oxygen-rich fluid. The fluid reservoir can in this case contain a gaseous, oxygen-containing fluid at high pressure. The pressure can preferably be at least 20 bar, preferably at least 50 bar, more preferably between 100 bar and 400 bar or more, even as much as 800 bar. In this way, a large amount of a gaseous fluid can be kept and stored in a small volume. In the case of a preferable adiabatic expansion of the gas, the temperature of the gas can be reduced sharply as it emerges from the fluid reservoir. In this way, a bypass flow at a sufficiently low temperature can be made available from the fluid reservoir. In addition, the internal pressure of the container may suffice to compensate for all system pressure losses and to supply a cooled, oxygen-containing gas flow from the fluid reservoir to the respiratory tract of a patient, without additional means for building up pressure.

In another embodiment of the present disclosure, the discharge flow and/or the cooling flow has an oxygen content of at least 20% by weight, wherein both flows can be deep-cooled, preferably liquefied air. However, the oxygen content can also be more than 50% by weight, more preferably over 90% by weight. It is also possible to use pure oxygen.

In one example, the discharge flow and/or the cooling flow has no additive gas components with a therapeutic effect. Apart from trace constituents, the discharge flow and/or the cooling flow can then only have oxygen and optionally nitrogen as components. A high oxygen fraction has a positive influence on the treatment of the patient, since oxygen saturation of the tissue can be easily obtained.

However, for management of patients, it is also possible to use oxygen-rich gases which have at least one additional, therapeutically active component, for example a noble gas such as argon and/or helium. However, vasodilators can also be used as an additional component, for example nitric oxide. Vasodilators are substances that expand the vessels and thus lower blood pressure. The addition of vasodilators can have a positive influence on the flow of blood through the tissue and therefore on heat transfer and on the temperature of the patient's tissue. Rapid and improved lowering of the body temperature can be achieved in particular by the combined use of at least one inert gas and at least one vasodilator as additional component of the oxygen-containing gas flow.

In one embodiment, the discharge flow of the oxygen-containing fluid and the cooling flow are provided from the storage device at substantially the same temperature level. The discharge flow and the cooling flow can be taken from a common line connected to the fluid reservoir of the storage unit. By means of a simple Y-pipe or by means of a three-way valve, two separate mass flows of the oxygen-containing fluid can be made available, of which one mass flow forms a bypass flow for cooling the other mass flow. A simple and cost-effective design of the device can be achieved in this way.

In another embodiment of the present disclosure, at least one preheater for preheating the discharge flow of the oxygen-containing fluid is provided upstream from the heat exchanger in the direction of flow of the discharge flow. The discharge flow is heated in the preheater from an exit temperature, upon emergence from the storage unit, to a temperature above the temperature of the cooling flow, in particular by heat transfer from the surroundings or surrounding air. The preheater can be configured as an atmospheric vaporizer which utilizes the energy of the surrounding atmosphere, i.e. the ambient air. This can in particular be provided if a liquefied, oxygen-containing gas is stored in the fluid reservoir. Suitable preheaters and/or vaporizers are known to persons skilled in the art. A heated, oxygen-containing gas flow then emerges from the preheater and is then cooled with a gaseous or optionally also liquid bypass flow of the cold, oxygen-containing gas from the fluid reservoir in order to obtain a defined low temperature for the supply of the oxygen-containing gas flow into the respiratory tract of the patient. With the aid of the preheater, it is easily possible to ensure that a sufficient temperature difference is obtained between the discharge flow and the cooling flow, which permits the exact adjustment of a desired temperature of the oxygen-containing gas flow. The temperature of the gas flow supplied to the patient can then be easily adjusted with the aid of the second, colder bypass flow.

In an advantageous embodiment of the present disclosure, the cooled, oxygen-containing gas flow is obtainable through an at least partial coming-together or mixing of the discharge flow and of the cooling flow. The two mass flows can in this case also be mixed completely with each other. In this way, a direct transfer of heat between the first mass flow and the second mass flow can be achieved, which leads to rapid and effective cooling of the discharge flow. A complete coming-together of the discharge flow and of the cooling flow additionally has the advantage that gas losses can be prevented. The fluid resources employed are thus utilized optimally.

In another advantageous embodiment of the present disclosure, between the preheater and the heat exchanger, at least one further heat exchanger can be provided for pre-cooling the discharge flow by indirect heat transfer to the cooling flow. If the cooling flow enters the further heat exchanger in a liquid state, the cooling flow can at least partially evaporate in the further heat exchanger on account of the heat transfer from the discharge flow.

The system according to the present disclosure has at least one stationary storage reservoir for filling the fluid reservoir of the device according to the present disclosure, wherein the system is designed to produce a releasable fluidic connection between the fluid reservoir and the storage reservoir for the purpose of refilling the fluid reservoir of the device from the storage reservoir.

The stationary storage reservoir, also called base unit, stores a large quantity of the oxygen-containing fluid, preferably at a high pressure, wherein a proportion of the fluid is preferably present as liquid phase. The fluid can be stored at a very high pressure of several 100 bar, preferably in excess of 400 bar. To refill the fluid reservoir of the device according to the present disclosure, the fluid reservoir is connected to the stationary storage reservoir. The connection can be safely obtained, for example, as a bayonet connection, screw connection or plug-in connection. The fluid reservoir of the transportable device is preferably refilled within a few minutes, preferably in less than 10 minutes, more preferably in less than five minutes, advantageously in approximately one minute. The stationary storage reservoir is configured in such a way that the stored fluid can be kept in store over a long period of time. The filling volume of the stationary storage reservoir is sufficiently large to allow the fluid reservoir of the transportable device to be completely filled several times. It is advantageous if the stationary storage reservoir stores a sufficient quantity of the oxygen-containing fluid to completely refill the fluid reservoir of the transportable device at least twice, more preferably at least five times, particularly preferably at least ten times.

A further aspect of the present disclosure, which if necessary can be combined with the above-described aspects of the present disclosure, additionally relates to a device for administering a cold gaseous composition to a mammal, wherein the gaseous composition comprises oxygen and at least one further gaseous and therapeutically active constituent, wherein the temperature of the gaseous composition during administration is less than 37° C., and the device has a gas container for storing the gaseous composition.

In an advantageous embodiment of the further aspect of the present disclosure, the gaseous and therapeutically active substance comprises an inert gas. In one embodiment, the gaseous and therapeutically active substance comprises argon.

In one example, the gaseous composition according to the further aspect of the present disclosure comprises oxygen in a proportion of at least 20%.

In an advantageous embodiment, according to the further aspect of the present disclosure, the cold gaseous composition is mixed with at least one other gas before the composition is administered to a mammal, wherein the temperature of the mixed gas is kept constant by means of an open-loop and/or closed loop control during the passage of the cold gaseous composition. The temperature is preferably adjusted with the aid of a passive actuator in the form of a bimetallic strip.

In an advantageous embodiment of the present disclosure, according to the further aspect of the present disclosure, provision can moreover be made that the through-flow of the cold gaseous composition is controlled by the bimetallic strip as a function of the temperature of the cold gaseous composition.

In one embodiment of the present disclosure, according to the further aspect of the present disclosure, the gaseous composition is stored in the gas container at a pressure of at least 800 bar. Furthermore, it is additionally or alternatively advantageous if the gaseous composition in the gas container has a temperature of less than −100° C.

In another embodiment, according to the further aspect of the present disclosure, the gaseous composition is cooled by a Peltier element before being supplied to the mammal.

In another embodiment, according to the further aspect of the present disclosure, the gaseous composition comprises a gaseous vasodilator, for example nitric oxide.

In this further aspect of the present disclosure, it may be advantageous to provide a connection element to a respiratory mask and/or to a ventilation tube.

According to the further aspect of the present disclosure, it is also expedient if electrical energy is generated using a Seebeck element with at least two connection points, wherein a first connection point is cooled by the cold gaseous composition, while a second connection point is at ambient temperature.

The above-described aspects of the present disclosure may if necessary be combined with one another, even if this is not expressly mentioned. The disclosure of the present disclosure is not limited to the combinations of inventive features predefined by the chosen paragraph formatting. In particular, a combination of the alternative embodiments described in the individual paragraphs is to be seen as advantageous and as being disclosed.

Further features of the present present disclosure will become clear from the following description of illustrative embodiments of the present disclosure and by reference to the drawing, and from the drawing itself. All of the features described here and/or shown in the drawings represent, either singly or in any desired combination, the subject matter of the present disclosure, and they do so independently of their presentation in the claims and of the back references indicated in the claims.

BRIEF DESCRIPTION OF THE DRAWINGS

The present disclosure is explained below with reference to the figures, in which.

DETAILED DESCRIPTION

Figure 1:
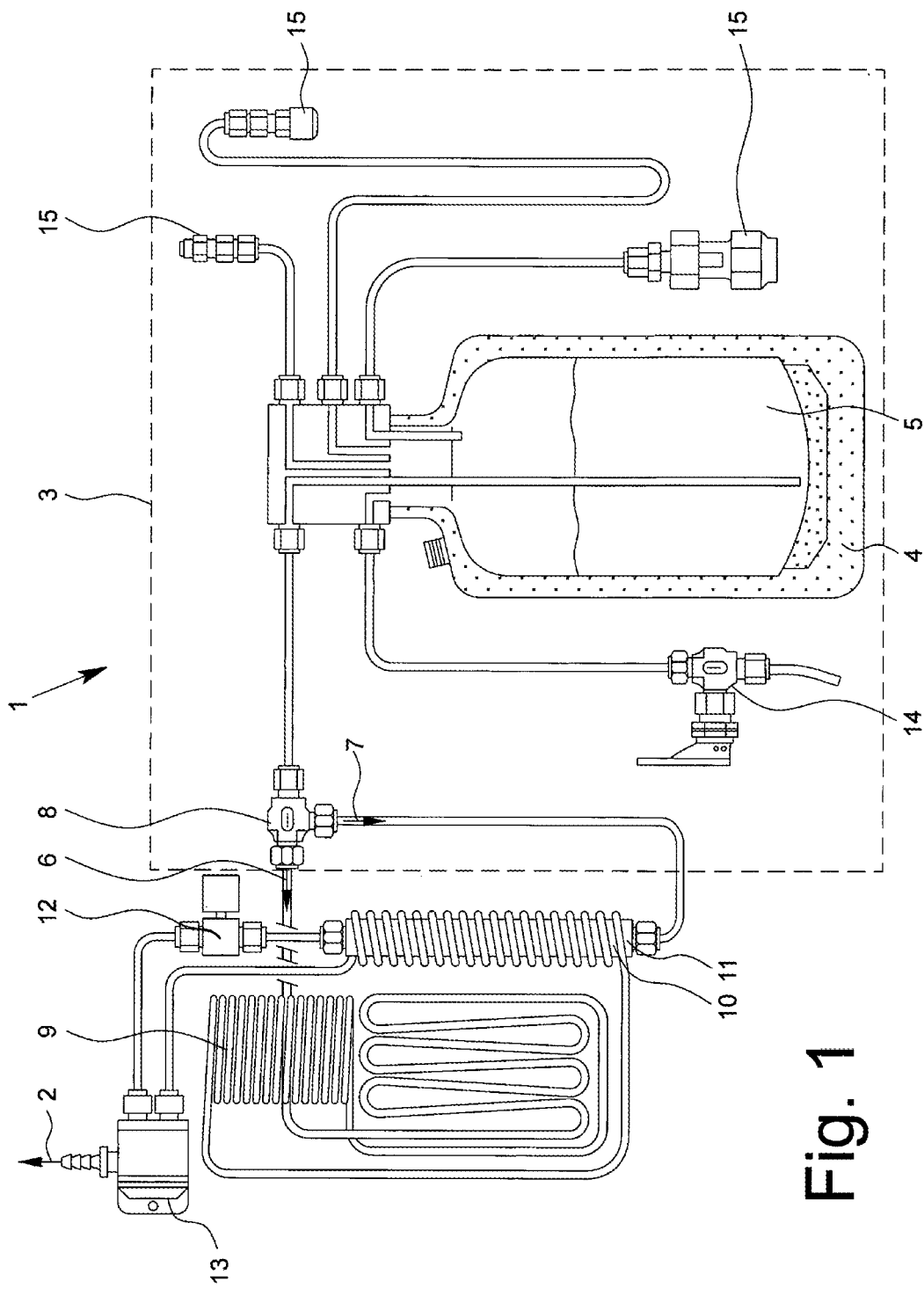
FIG. 1 shows a schematic view of a transportable device for providing a cooled, oxygen-containing gas flow for supply to a body of a mammal via the respiratory tract, in particular of a human being, in order to lower the body temperature.

FIG. 1 shows a transportable device 1 for providing a cooled, oxygen-containing gas flow 2 for supply to a body (not shown) of a mammal via the respiratory tract, in particular of a human being, in order to lower the body temperature. The transportable device 1 has a storage unit 3 comprising at least one fluid reservoir 4. The fluid reservoir 4 stores at least one oxygen-containing fluid 5, which is preferably stored as cold liquefied gas in the fluid reservoir 4 of the storage unit 3. In contrast to what is shown in FIG. 1, the storage unit 3 can also have more than one fluid reservoir 4, in which case the different fluid reservoirs 4 can store different fluids 5 or else the same fluids 5.

The storage unit 3 provides a discharge flow 6 of an oxygen-containing fluid 5 and a cooling flow 7 of the fluid 5. The two mass flows 6, 7 are removed from the fluid reservoir 4 via a common conduit and a common valve. A three-way valve 8 of the storage unit 3 divides the common mass flow into the first mass flow 6 and the second mass flow 7. The valve 8 can also be configured as a Y-pipe. The valve 8 can be designed to be switchable and/or controllable in an closed-loop manner, as a result of which the mass flows 6, 7 can be changed.

The discharge flow 6 is conveyed through a preheater 9. If the fluid 5 is a cold, liquefied gas, the preheater 9 can be configured as an atmospheric vaporizer. The energy needed to vaporize the liquefied gas is in this case taken from the ambient air. The pressure increases during the vaporization, such that system pressure losses are overcome and the supply of the cold, oxygen-containing gas flow 2 into the respiratory tract of a patient is ensured even without additional conveying means such as compressors or fans. On emerging from the preheater 9, the discharge flow 6 then has a temperature above the temperature of the cooling flow 7.

On account of a heat transfer from the environment into the fluid container 4, the internal pressure of the container can also increase, such that the internal pressure of the container may on its own be sufficient to overcome system pressure losses, and the supply of the cold, oxygen-containing gas flow 2 into the respiratory tract of a patient is ensured.

An indirect heat exchanger 10 can be arranged downstream from the preheater 9, in which case heat is transferred from the discharge flow 6 to the cooling flow 7, and the discharge flow 6 is cooled. To improve the heat transfer in the heat exchanger 10, a metallic mass 11 with a high heat capacity can be provided. By means of the metallic mass, the heat transfer can be improved and kept at a constant level. Examples of materials that can be used for the metallic mass are copper or brass. However, embodiments of the device 1 according to the present disclosure are conceivable in which no indirect heat exchanger 10 is provided.

The size of the cooling flow 7 is controlled and/or regulated by an actuator of an open-loop and/or closed-loop controller 12. The actuator can be configured as an actively switched valve. To switch the valve, the actual temperature of the oxygen-containing gas flow 2 is measured, then compared with a desired value, and the active actuator 12 is switched accordingly. In an advantageous embodiment, the actuator 12 is a passive actuator. As passive actuator 12, it is possible to use a bimetallic strip which changes its shape when the temperature around the bimetallic strip changes, as a result of which the size of the cooling flow 7 can be changed by means of the actuator 12. The cooling of the discharge flow 6 in the heat exchanger 10 can be influenced by a change in the mass ratios of discharge flow 6 and cooling flow 7.

The discharge flow 6 is then fed to a direct heat exchanger 13. In the heat exchanger 13, the discharge flow 6 and the cooling flow 7 are brought together preferably completely or else just partially. Fractions of the gas flows 6 and 7 that are not brought together can be let out to the environment. By means of the discharge flow 6 mixing with the cooling flow 7, the temperature of the discharge flow 6 is preferably further reduced, such that a cooled, oxygen-containing gas flow 2 is provided at a defined, therapeutically active temperature below the body temperature. In principle, a temperature equalization of the discharge flow 6 and of the cooling flow 7 can already take place in the first heat exchanger 10, such that mass flows 6, 7 at substantially the same temperature can be brought together in the direct heat exchanger 13.

In one example, the discharge flow 6 and the cooling flow 7 are mixed together completely with each other in the direct heat exchanger 13, such that no fluid 5 is released to the environment.

The fluid reservoir 4 shown in FIG. 1 is refillable. For this purpose, the fluid reservoir 4 has a hose and/or pipe connection to an admission valve 14. The admission valve 14 can be connected to a stationary storage reservoir (not shown). The fluid reservoir 4 can be refilled in a simple manner via the admission valve 14.

Furthermore, the transportable device 1 has safety features (known per se) for safely storing and safely operating the device, for example the safety valves 15 shown.

Figure 2:
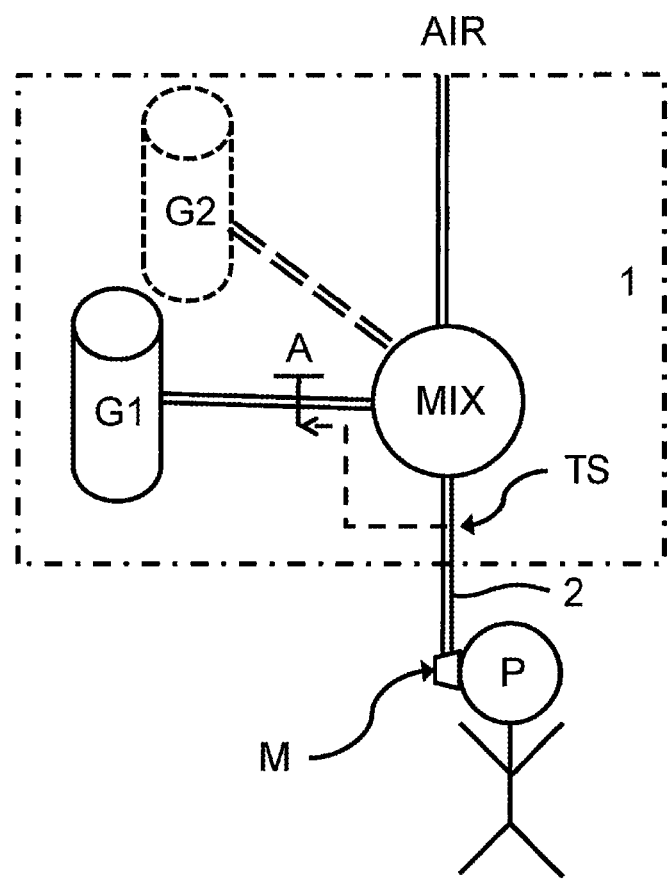
FIG. 2 shows a schematic view of an alternative embodiment of a transportable device for providing a cooled, oxygen-containing gas flow for supply to a body of a mammal.

FIG. 2 shows an alternative embodiment of a transportable device 1 for providing a cold gaseous composition to a mammal. The transportable device 1 has at least one gas container G1 for storing a gaseous composition. The gaseous composition consists of oxygen and at least one other gaseous, therapeutically active constituent. The gaseous, therapeutically active constituent is intended to reduce the oxygen consumption and/or to improve the blood flow in the body of the patient.

The device 1 can be used both for active and also passive ventilation.

In addition to the first gas container G1, the device 1 can have a second gas container G2 with a second gas or a second gaseous composition. Ambient air is mixed with the gas composition from the first gas container G1 in a mixing chamber MIX. If a second gas or a second gaseous composition from a further gas container G2 is used, this gas too is conveyed into the mixing chamber MIX. The mixed gas is then fed to the respiratory tract of a patient P via a mask M. The gaseous composition is cooled on account of adiabatic expansion as it leaves the container G1. The temperature of the gas flow 2 supplied to the patient can be adjusted with the aid of the cooled gaseous composition. To adjust the temperature of the gas flow 2, a valve A is provided, which adjusts the through-flow of the gaseous composition. For this purpose, the temperature TS of the gas flow 2 is used as control variable for the valve A. The temperature can be converted by a temperature-sensitive element, for example a bimetallic strip, into an actuation of the valve A. If the temperature TS of the gas flow 2 falls, the valve A is switched in such a way that the through-flow of the gaseous composition is reduced. If the temperature TS of the gas flow 2 rises, then, by analogy, the through-flow of the gaseous composition is accordingly increased by the valve A.

Alternatively, an actively switched valve A can also be used to regulate the through-flow of the gaseous composition. In this case, the device 1 can contain a Seebeck element (not shown) that provides the required energy.

Figure 3:
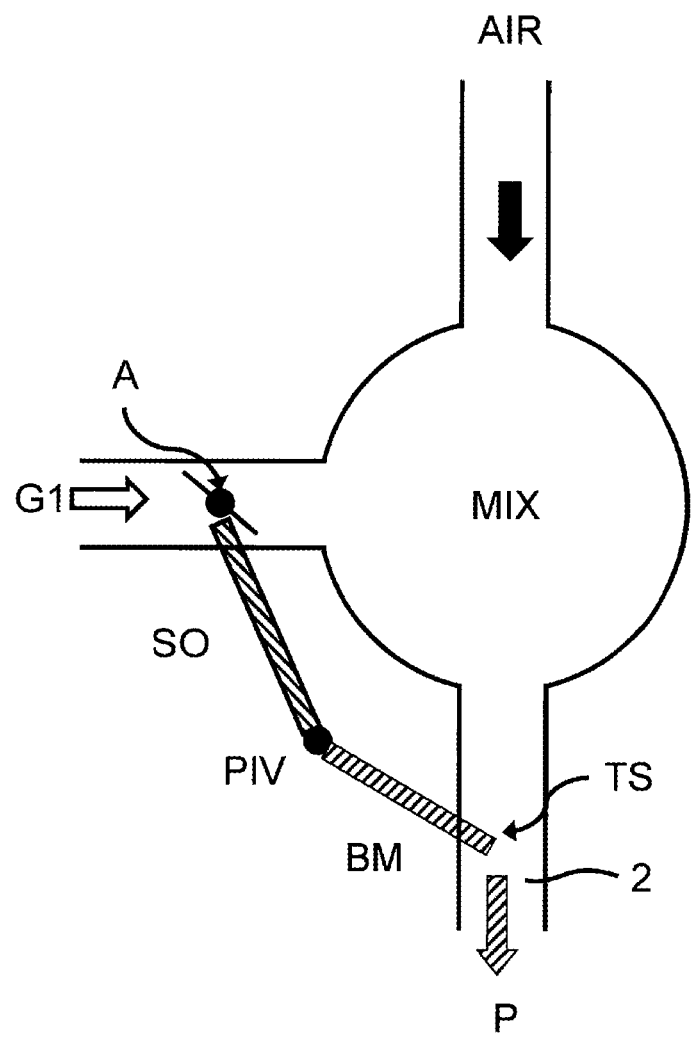
FIG. 3 shows a schematic view of a passive temperature regulation by means of a bimetallic strip in the transportable device from FIG. 2.

FIG. 3 is a schematic view of a detail of the mixing chamber MIX and shows the way in which the passive valve A functions. An air flow from the ambient air AIR is delivered to the mixing chamber MIX. In addition, a mass flow of a gaseous composition from a gas container G1 is delivered to the mixing chamber MIX. A cold, oxygen-containing gas flow 2 emerges from the mixing chamber MIX in order to be supplied to a patient P. The temperature TS of the emerging gas flow serves as an input control variable for the switching of the valve A. The gas flow 2 circulates around a bimetallic strip BM. The bimetallic strip BM is connected via a fastening point PIV to a lever arm SO, which adjusts the valve A. If the temperature TS of the gas flow 2 falls, this leads to a change of geometry of the bimetallic strip BM, in such a way that the lever arm SO is moved such that the valve A is opened wider, as a result of which the temperature TS of the gas flow is lowered. Analogously, the opposite is the case if the temperature TS of the gas flow 2 falls.

Figure 4:
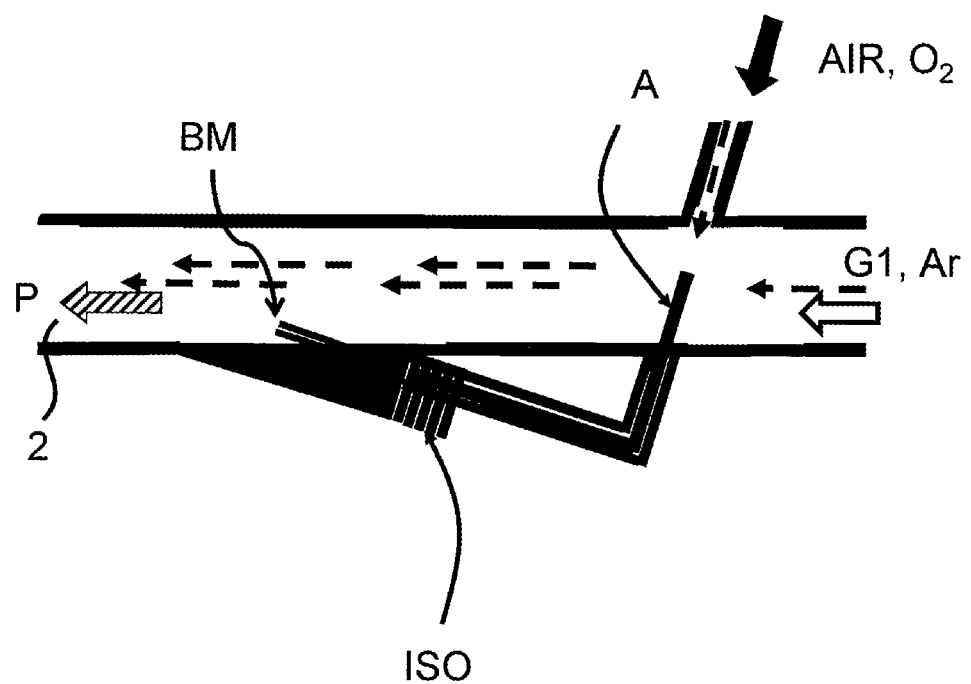
FIG. 4 shows a schematic view of an alternative embodiment of a passive temperature regulation by means of a bimetallic strip.

FIG. 4 shows an alternative embodiment of a mixing chamber with a valve A for controlling the temperature of a gas flow 2. The valve A is connected by an insulator ISO to a bimetallic strip BM around which the gas flow 2 circulates at least in part. A change of temperature of the gas flow 2 causes a change of position of the valve A, as a result of which the temperature of the gas flow 2 is adjusted to a desired temperature.

Figure 5:
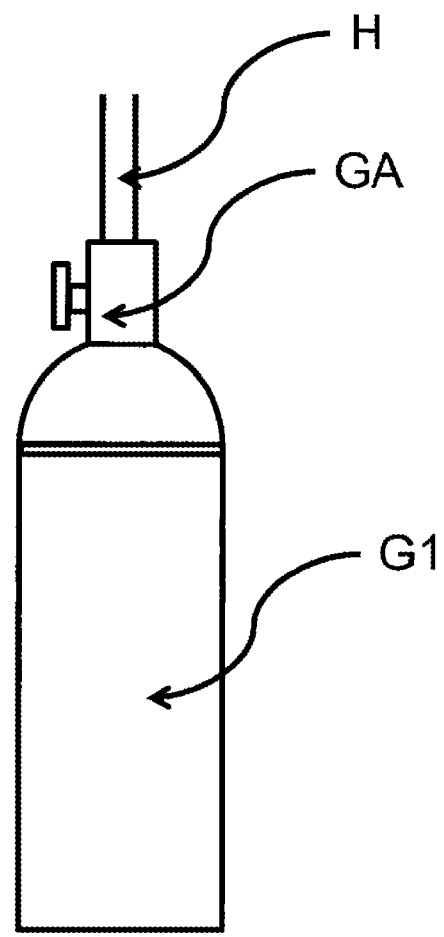
FIG. 5 shows a schematic view of a gas container of the device shown in FIG. 2.

FIG. 5 shows a gas container G1 having a gaseous composition at a temperature of less than −60° C., preferably at a temperature of less than −100° C., more preferably at a temperature at which the gaseous composition in the gas container G1 is liquefied. Accordingly, the gaseous composition in the gas container G1 preferably has a temperature of −183° C.

Figure 6:
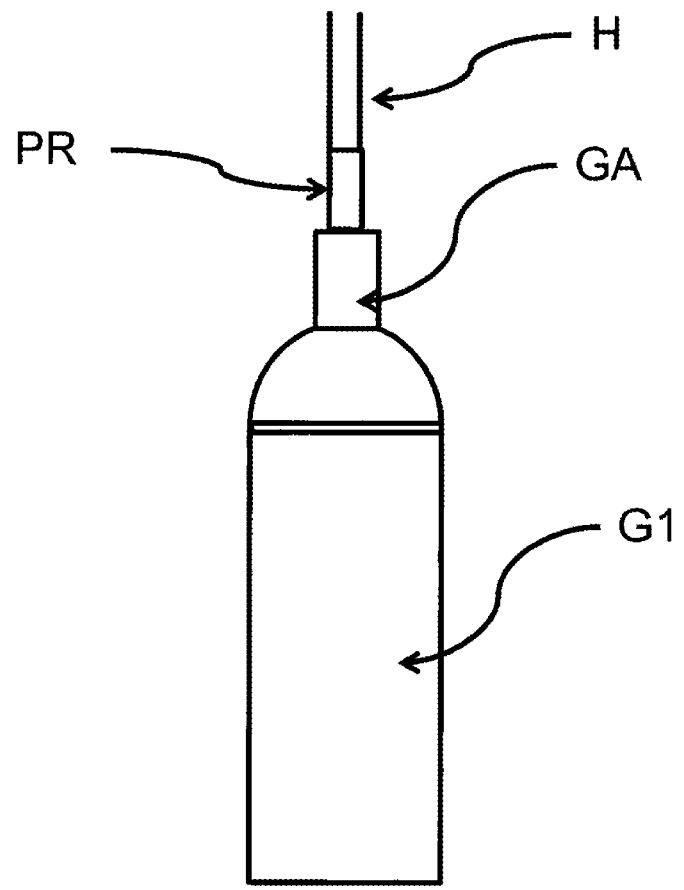
FIG. 6 shows a schematic view of an alternative embodiment of a gas container.

An alternative embodiment of the gas container G1 is shown in FIG. 6. The gas container G1 stores the gaseous composition at a pressure of at least 800 bar. Upon the adiabatic expansion of the gaseous composition via a pressure-reducing valve PR, the gaseous composition is cooled. On account of the great pressure difference, there is therefore no need for a cooling element for cooling the gaseous composition. The connecting pipe H can be configured as a pressure-measuring instrument GA or can contain a measuring instrument for pressure measurement. After the expansion, the gaseous composition is preferably at approximately normal pressure. The gaseous composition can still be liquefied or have a liquefied fraction.

Since the gaseous composition is stored at a low temperature or a high pressure in the gas container G1, it is possible to dispense with a cooling element, for example a Peltier element.

LIST OF REFERENCE SIGNS

1 device
2 gas flow
3 storage unit
4 fluid reservoir
5 fluid
6 mass flow
7 mass flow
8 valve
9 preheater
10 heat exchanger
11 mass
12 closed-loop controller
13 heat exchanger
14 admission valve
15 safety valve
MIX mixing chamber
G1 gas container G2 gas container
AIR air
TS temperature
P patient
M mask
A valve
ISO insulator
PR valve

The invention claimed is:

1. A transportable device for providing a cooled, oxygen-containing gas flow for supply to a body of a human being via the respiratory tract in order to lower the body temperature, the transportable device comprising:
a storage unit, which has at least one fluid reservoir; and
at least one heat exchanger;
wherein the storage unit is designed to store an oxygen-containing fluid in the fluid reservoir and to provide a discharge flow of the oxygen-containing fluid from the fluid reservoir;
wherein the heat exchanger is designed to cool the provided discharge flow by transferring heat to a cooling flow of a stored fluid provided by the storage unit;
wherein a cooled, oxygen-containing gas flow for supply to the body emerges from the heat exchanger;
wherein the cooling flow is formed by a bypass flow of the oxygen-containing fluid stored in the fluid reservoir;
wherein the fluid reservoir contains a deep-cooled, liquefied oxygen-containing fluid or a pressurized oxygen-rich fluid as the cooling flow; and
wherein the cooling flow of the deep-cooled, liquefied oxygen-containing fluid or the pressurized oxygen-rich fluid is not cooled by external means before being provided to the heat exchanger.

2. The transportable device as claimed in claim 1, wherein an open-loop and/or closed-loop controller is provided which is designed to permit open-loop and/or closed-loop control of the temperature of the cooled, oxygen-containing gas flow by changing the size of the cooling flow.

3. The transportable device as claimed in claim 1, wherein the fluid reservoir contains liquid oxygen or liquefied air.

4. The transportable device as claimed in claim 1, wherein the discharge flow and/or the cooling flow has an oxygen content of at least 20% by weight.

5. The transportable device as claimed in claim 1, wherein the discharge flow and the cooling flow are provided by the storage unit at the same temperature level.

6. The transportable device as claimed in claim 1, wherein at least one preheater for preheating the discharge flow is provided upstream from the heat exchanger in the direction of flow of the discharge flow, wherein the discharge flow is heated in the preheater from an exit temperature, upon emergence from the storage unit, to a temperature above the temperature of the cooling flow, in particular by heat transfer from the environment.

7. The transportable device as claimed in claim 6, wherein, between the preheater and the heat exchanger, at least one further heat exchanger is provided for precooling the discharge flow by indirect heat transfer to the cooling flow.

8. The transportable device as claimed in claim 1, wherein the cooled, oxygen-containing gas flow is obtainable through an at least partial coming-together of the discharge flow and of the cooling flow.

9. The transportable device as claimed in claim 1, wherein the heat exchanger is designed for direct heat transfer between the discharge flow and the cooling flow by mixing-together of the discharge flow and the cooling flow.

10. A system having at least one device as claimed in claim 1 and having a stationary storage reservoir for filling the fluid reservoir of the device, designed to produce a releasable fluidic connection between the fluid reservoir and the storage reservoir for the purpose of refilling the fluid reservoir of the device from the storage reservoir.

11. A method for lowering the body temperature of a human being via the respiratory tract by means of a cold, oxygen-containing gas, said method being carried out with the transportable device of claim 1, wherein a cold, liquefied gas is heated in a first subsidiary flow and is then mixed with a second, cold bypass flow, as a result of which the temperature of the gas is subject to open-loop and/or closed-loop control.

12. A method for providing a cooled, oxygen-containing gas flow for supply to a body of a human being via the respiratory tract in order to lower the body temperature, said method being carried out with a device which has a storage unit, comprising at least one fluid reservoir, and which has at least one heat exchanger and an open-loop and/or closed loop controller, wherein an oxygen-containing fluid is stored in the fluid reservoir, and a discharge flow of the oxygen-containing fluid is provided, wherein the discharge flow is cooled in the heat exchanger by transfer of heat to a cooling flow of a fluid stored in and provided by the storage unit, and wherein a cooled, oxygen-containing gas flow for supply to the body emerges from the heat exchanger;
wherein the cooling flow is formed by a bypass flow of the oxygen-containing fluid stored in the fluid reservoir;
wherein the fluid reservoir contains a deep-cooled, liquefied oxygen-containing fluid or a pressurized oxygen-rich fluid as the cooling flow; and
wherein the cooling flow of the deep-cooled, liquefied oxygen-containing fluid or the pressurized oxygen-rich fluid is not cooled by external means before being provided to the heat exchanger.

13. A transportable device for providing a cooled, oxygen-containing gas flow for supply to a body of a human being via the respiratory tract in order to lower the body temperature, the transportable device comprising:
a storage unit, which has at least one fluid reservoir; and
at least one heat exchanger;
wherein the storage unit is designed to store an oxygen-containing fluid in the fluid reservoir and to provide a discharge flow of the oxygen-containing fluid from the fluid reservoir;
wherein the heat exchanger is designed to cool the provided discharge flow by transferring heat to a cooling flow of a stored fluid provided by the storage unit;
wherein a cooled, oxygen-containing gas flow for supply to the body emerges from the heat exchanger;
wherein at least one preheater for preheating the discharge flow is provided upstream from the heat exchanger in the direction of flow of the discharge flow, wherein the discharge flow is heated in the preheater from an exit temperature, upon emergence from the storage unit, to a temperature above the temperature of the cooling flow by heat transfer from the environment; and
wherein, between the preheater and the heat exchanger, at least one further heat exchanger is provided for precooling the discharge flow by indirect heat transfer to the cooling flow.

* * * * *